United States Patent

Low et al.

Patent Number: 5,321,184
Date of Patent: Jun. 14, 1994

[54] PRETREATMENT METHOD FOR C$_8$ AROMATIC ISOMERIZATION PROCESS

[75] Inventors: Chi-Chu D. Low, Lisle; Randy J. Lawson, Palatine; Paul J. Kuchar, Hinsdale, all of Ill.; Gail L. Gray, London, England

[73] Assignee: UOP, Des Plaines, Ill.

[21] Appl. No.: 997,831

[22] Filed: Dec. 29, 1992

[51] Int. Cl.$^5$ ............................................. C07C 5/22
[52] U.S. Cl. .................................. 585/481; 585/477; 585/482
[58] Field of Search .................... 585/477, 481, 482

[56] References Cited

U.S. PATENT DOCUMENTS

| | | |
|---|---|---|
| 3,078,318 | 2/1963 | Berger . |
| 3,997,618 | 12/1976 | Cornely et al. ............... 585/482 |
| 4,140,624 | 2/1979 | Masologites .................. 585/482 |
| 4,188,282 | 2/1980 | Tabak et al. ................. 585/481 |
| 4,899,012 | 2/1990 | Sachtler et al. ............... 585/481 |

OTHER PUBLICATIONS

Meyers, Robert A., *Handbook of Refining Petroleum Processes*, pp. 5-68 to 5-70, McGraw-Hill, Inc. (1986).

Primary Examiner—Patrick P. Garvin
Assistant Examiner—E. D. Irzinski
Attorney, Agent, or Firm—Thomas K. McBride; John F. Spears, Jr.; Reginald K. Taylor

[57] ABSTRACT

A pretreatment method for a C$_8$ aromatic isomerization process wherein the isomerization catalyst is initially contacted with a C$_8$ aromatic feedstock under high severity isomerization conditions for a period of time sufficient to deposit a substantial amount to carbonaceous material on the catalyst. After pretreatment, the carbon-laden catalyst continues to be contacted by the C$_8$ aromatic feedstock under less severe conditions than that of the pretreatment mode of operation.

22 Claims, 1 Drawing Sheet

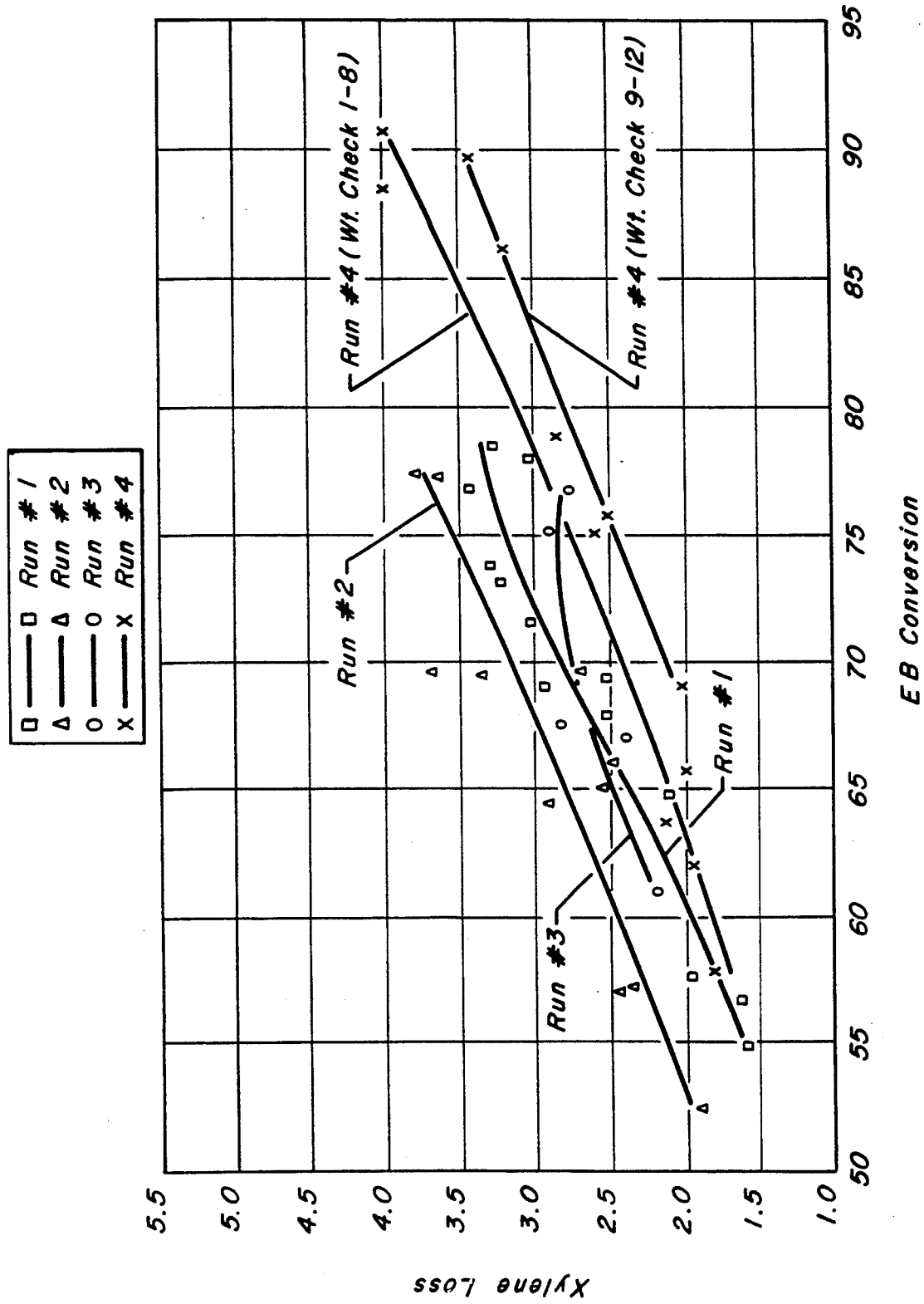

PRETREATMENT METHOD FOR C₈ AROMATIC ISOMERIZATION PROCESS

FIELD OF THE INVENTION

The present invention relates to a pretreatment method for a $C_8$ aromatic isomerization process. More specifically, the present invention involves pretreating an isomerization catalyst by contacting the catalyst with a $C_8$ aromatic feedstock under high severity isomerization conditions for a period of time sufficient to deposit a substantial amount of carbonaceous material on the catalyst.

BACKGROUND OF THE INVENTION

Para-xylene and ortho-xylene are important petrochemical intermediates that are used to produce end products such as polyester fibers and film, plasticizers, polyester, and alkyd resins.

Currently, para-xylene is produced mainly by the isomerization of the isomeric $C_8$-aromatic hydrocarbons, namely ortho-xylene, meta-xylene, and ethylbenzene, or nonequilibrium mixtures of these isomers (including para-xylene) thereof, into the para-xylene isomer. The isomerization is typically effected by contacting the $C_8$ hydrocarbons, in admixture with hydrogen, with a dual function catalyst possessing both hydrogenation and cracking activities, thereby effecting the desired isomerization reaction. Common operating conditions are temperatures from about 0°–700° C., pressures of about atmospheric to 100 atmospheres, and a hydrogen to hydrocarbon mole ratio of about 0.5–25.

An example of a $C_8$ aromatic isomerization process is U.S. Pat. No. 3,078,318 (issued to Berger). The Berger patent discloses a process for the selective production of a particular isomer which comprises subjecting a $C_8$ aromatic hydrocarbon fraction to isomerization in the presence of a catalyst comprising platinum on alumina, and thereafter separating out a particular xylene from the resulting hydrocarbon mixture. Further, the Berger patent teaches that after removal of a particular isomer from a mixture of $C_8$ aromatic hydrocarbons, the remaining isomeric components in the mixture may be subjected to isomerization in the presence of hydrogen and a catalyst comprising a Group VIII metal on alumina to regenerate the mixture of $C_8$ aromatic hydrocarbon isomers and approach the equilibrium proportions of ortho-, meta-, and para-xylenes and ethylbenzene.

In Meyers, Robert A., *Handbook of Petroleum Processes*, pages 5–68 to 5–70, McGraw-Hill, Inc. (1986), an integrated xylene isomerization process is described. In this process, a deheptanized $C_8$ aromatic feedstock containing a mixture of $C_8$ xylene isomers and ethylbenzene is passed to a xylene splitter fractionation unit to remove heavy aromatics and recover the desired amount of ortho-xylene product. The overhead from this column goes to the para-xylene recovery section. Effluent, depleted in para-xylene, exits from the xylene recovery unit and is directed to the isomerization unit where xylene isomers are isomerized to equilibrium and ethylbenzene is converted to benzene and ethane. The effluent from the isomerization reactor is separated into a hydrogen-rich vapor and a liquid phase which is passed to a deheptanizer to remove $C_7$ minus products.

In the isomerization reactor, ethylbenzene reacts to produce benzene and ethane and the nonequilibrium xylene isomer mixture moves towards equilibrium. During the course of these reactions, there is some loss of xylenes by transalkylation and dealkylation to other aromatics, for example, toluene and $C_9$ aromatics. Further, there are additional xylene losses due to cracking and saturation of $C_8$ aromatics. It is important to reduce the xylene losses in the isomerization reactor because this reduces feedstock requirements for the xylene isomerization process and increases the proportion of higher-valued products that can be recovered.

In the past, the problem of xylene losses due to side reactions occurring in the isomerization reactor was addressed by manipulating catalyst formulations to increase selectivity (xylene retention) of the $C_8$ aromatic isomerization process. Numerous catalysts for isomerizing $C_8$ aromatics have been disclosed, and many of them involve the use of crystalline-aluminosilicate compounds known as zeolites. Zeolites particularly suited for isomerization include mordenite and the ZSM variety. In addition to the zeolite component, certain metal promoters and inorganic oxide matrices have been included in isomerization catalyst formulation. Examples of inorganic oxides include silica, alumina, and mixtures thereof. Metal promoters, such as Group VIII or Group III metals, have been used to provide a hydrogenation functionality.

Another method disclosed for reducing the xylene loss in a $C_8$ aromatic isomerization process is isomerizing at less severe operating conditions. The problem with this approach is that a reduction in ethylbenzene conversion per pass usually results when these less severe operating conditions are employed.

There is a need for a method for reducing the xylene losses that accompanies $C_8$ aromatic isomerization while maintaining high ethylbenzene conversion.

SUMMARY OF THE INVENTION

It has been discovered that a pretreatment method can reduce xylene losses in a $C_8$ aromatic isomerization process without sacrificing ethylbenzene conversion. The method involves contacting an isomerization catalyst with a $C_8$ aromatic hydrocarbon feedstock under high severity isomerization conditions for a period of time sufficient to deposit a substantial amount of carbonaceous material on the catalyst. Although not wanting to be limited to theory, it is believed that the reduction in xylene losses is caused by the initial carbon lay-down on the catalytic metal site which further attenuates its metal function, thereby reducing the hydrogenation function of the catalyst.

The present invention is a method of isomerizing $C_8$ aromatics to a product stream comprising xylenes which comprises the steps of: introducing a $C_8$ aromatic feedstock comprising a nonequilibrium mixture of at least one xylene isomer in admixture with ethylbenzene into an isomerization zone in the presence of an isomerization catalyst under high severity isomerization conditions for a period of time sufficient to deposit a carbon content of at least about 0.1 wt. % on the catalyst; continuing to contact the $C_8$ aromatic feedstock in the isomerization zone in the presence of the resulting catalyst under moderate severity isomerization conditions; and recovering the product stream.

In another embodiment, the present invention is a method for isomerizing $C_8$ aromatics into a product stream comprising xylenes which comprises the steps of: introducing a $C_8$ aromatic feedstock comprising a nonequilibrium mixture of xylene isomers in admixture with ethylbenzene into an isomerization zone in the presence of an isomerization catalyst under high severity isomerization conditions sufficient to effect a first ethylbenzene conversion for a period of time sufficient to deposit a substantial amount of carbonaceous material on the catalyst; continuing to contact the $C_8$ aromatic feedstock in the isomerization zone in the presence of the resulting catalyst under moderate severity isomerization conditions sufficient to effect a second ethylbenzene conversion, the second ethylbenzene conversion being lower than the first ethylbenzene conversion; and recovering the product stream.

In another embodiment, the present invention is a method for isomerizing $C_8$ aromatics to a product stream comprising xylenes comprising the steps of: introducing a $C_8$ aromatic feedstock comprising a nonequilibrium mixture of xylene isomers in admixture with ethylbenzene into an isomerization zone in the presence of a catalyst comprising a Group VIII metal and a lead component deposited on a zeolite composite support under high severity isomerization conditions sufficient to effect an ethylbenzene conversion of at least about 80% for 10-24 hours to deposit at least about 0.1 wt. % carbon on the catalyst; continuing to contact the $C_8$ aromatic feedstock in the isomerization zone in the presence of the resulting catalyst under moderate severity isomerization conditions sufficient to effect an ethylbenzene conversion of not more than about 65%; and recovering the product stream.

In another embodiment, the present invention is a method for isomerizing $C_8$ aromatics to a product stream comprising xylenes comprising the steps of: introducing a $C_8$ aromatic feedstock comprising a nonequilibrium mixture of xylene isomers in admixture with ethylbenzene into an isomerization zone in the presence of catalyst comprising a combination of a Group VIII metal component and a lead component deposited on a carrier material comprising a pentasil zeolite and an inorganic oxide binder under high severity isomerization conditions sufficient to effect an ethylbenzene conversion of at least 90% for 10-24 hours to deposit at least about 0.2 wt. % carbon on the catalyst; continuing to contact the $C_8$ aromatic feedstock in the isomerization zone in the presence of the resulting catalyst under moderate severity isomerization conditions sufficient to effect an ethylbenzene conversion of not more than about 65%; and recovering the product stream.

BRIEF DESCRIPTION OF THE DRAWING

The FIGURE is a plot of ethylbenzene conversion versus xylene losses for $C_8$ aromatic isomerization process runs using moderate start-up conditions (Runs 1-3) and a $C_8$ aromatic isomerization process using the high severity start-up procedure of the present invention (Run No. 4).

BRIEF DESCRIPTION OF THE PREFERRED EMBODIMENTS

The present invention involves a xylene isomerization pretreatment process that introduces a $C_8$ aromatic feedstock into an isomerization zone in the presence of an isomerization catalyst under high severity isomerization conditions for a period of time sufficient to deposit a substantial amount of carbonaceous material on the catalyst. After this pretreatment, contacting of the resulting carbon-laden isomerization catalyst with the $C_8$ aromatic feedstock continues, but at a severity significantly lower than that experienced in the pretreatment mode of operation.

$C_8$ aromatic hydrocarbons suitable for use as feedstocks for the present invention generally include certain hydrocarbon fractions containing at least one of the $C_8$ aromatic hydrocarbon isomers. The feedstock may thus be a single $C_8$ aromatic hydrocarbon such as one of the group consisting of ortho-, meta-, or para-xylene or ethylbenzene, or any mixture thereof in which the ratio of isomers is other than the equilibrium proportion of $C_8$ aromatic hydrocarbon components. The feedstock may also contain other hydrocarbon classes such as paraffins, olefins, and naphthenes. Although other hydrocarbon classes maybe present in the feedstock of the present invention, it is preferred that the mixture contain no substantial proportion of polymerizable or condensable hydrocarbons. In a preferred embodiment, the source of the $C_8$ aromatic-containing feedstock is a fraction derived from certain petroleum conversion products containing aromatic hydrocarbons and including fractions boiling within the range of about 120°-145° C. Suitable fractions utilizable as a feedstock in the present process may be separated from gasoline produced by subjecting an appropriately boiling petroleum fraction to dehydrogenation, as for example, a hydroformed gasoline boiling range fraction containing naphthenic hydrocarbons. Such gasoline boiling range fractions of petroleum conversion products may be produced either thermally and/or produced in a catalyzed cracking, reforming, or hydroforming unit.

The catalyst of the present invention can be any suitable isomerization catalyst known to those skilled in the art. The catalyst will typically comprise an acidic inorganic oxide support which has incorporated at least one metallic component.

With respect to the inorganic oxide binder utilized in the present invention, it is preferred that the binder be a porous, adsorptive, high surface area support having a surface area of about 25-500 m$^2$/g. The binder should also be uniform in composition and relatively refractory to the conditions utilized in the isomerization process of the present invention. Examples of suitable binders include alumina, silica, silica-alumina, zinc, titanium, zirconium, magnesia, thoria, chromia, boria, attapulgus clay, diatomaceous earth, Fuller's earth, kaolin, kieselguhr, and any mixtures thereof. The preferred binder is alumina. Suitable aluminas are the crystalline aluminas known as gamma, beta, and theta. The preferred alumina is gamma alumina. Preferred binders have an apparent bulk density of about 0.3 to about 0.8 g/cc and surface area characteristics such that the average pore diameter is about 20-300 Angstroms and the pore volume is about 0.1-1 cc/g.

With respect to the metallic component, the preferred metal is a Group VIII metal. Suitable Group VIII metals include platinum, palladium, rhodium, ruthenium, osmium, and iridium, preferably platinum. The Group VIII metal may exist within the final catalyst as an oxide, sulfide, halide, oxysulfide, or as an elemental metal, or as any combination thereof. The Group VIII metal component generally comprises about 0.01-2 wt. % of the final component, preferably 0.05-1.0 wt. %.

The Group VIII metal component may be incorporated into the catalyst composite of the present invention using any suitable means that results in the metal distribution that is disclosed herein. Suitable examples are ion exchange and impregnation. The preferred method of preparing the catalyst normally involves the use of a water-soluble decomposable compound of a Group VIII metal to impregnate a calcined zeolite/binder composite. For example, the Group VIII metal may be added to a calcined hydrogel by commingling the calcined composite with an aqueous solution of chloroplatinic or chloropalladic acid.

In a preferred embodiment, the catalyst of the present invention contains a lead component. The lead component may be incorporated into the catalytic composite in any suitable manner to effectively disperse this component on the individual moieties of the composite and to achieve the disclosed distribution of lead between the zeolite moiety and the binder moiety. A suitable method can include coprecipitation or cogelation with the inorganic oxide binder, ion-exchange with the inorganic oxide binder, or impregnation of the catalyst at any stage of precipitation. One preferred method of incorporating the lead component into the catalytic composite involves the addition of suitable soluble lead compounds such as lead nitrate, lead acetate, lead citrate, lead formate, and the like to the zeolite-containing hydrosol of the inorganic oxide, and then combining the hydrosol with a suitable gelling agent and dispersing the resulting mixture into an oil bath. After calcining the gelled hydrosol, there is obtained a binder material having a uniform dispersion of lead oxide in intimate combination principally with the inorganic binder.

Another preferred method of incorporating the lead component into the catalyst composite involves the use of a soluble, decomposable compound of lead to impregnate and uniformly disperse the lead on the composite. In general, the lead component can be impregnated prior to, simultaneously with, or after the Group VIII metal is added to the carrier.

In another embodiment, the catalyst of the present invention contains a halogen component. The halogen is combined with the carrier material or with the other ingredients of the catalyst in the form of the corresponding halide. Suitable halogens include chlorine, iodine, bromine, or any mixtures thereof, preferably fluorine and chlorine. The halogen may be added to the carrier material in any suitable manner known to those skilled in the art either during preparation of the carrier material or before or after the addition of the other components.

Regardless of how the catalyst components are combined with the porous carrier material, the catalyst composite will be dried at a temperature of from about 100°-320° C. for a period of about 2-24 hours. The desired composite is then calcined at a temperature of about 400°-600° C. in air at atmospheric conditions for a period of about 0.1-10 hours to convert the metallic compounds substantially to the oxide form. The resultant calcined composite may be subjected to a substantially water-free reduction step prior to its use in the conversion of hydrocarbons. The reducing agent, which is preferably hydrogen, contacts the catalyst at conditions including a temperature of about 200°-650° C. for a period of about 0.5-10 hours to reduce substantially all of the Group VIII metal components to the metallic state.

In a preferred embodiment, the catalyst of the present invention comprises a Group VIII metal, a lead component sufficient to amount to an atomic ratio of lead to Group VIII metal from about 2-10, from about 1-20 wt. % of a pentasil zeolite, and an inorganic binder, wherein from about 80-100 wt. % of the Group VIII metal and about 60-100 wt. % of the lead component are contained in the inorganic binder.

In accordance with the present invention, a $C_8$ aromatic feedstock is contacted with an isomerization catalyst, both described hereinabove, in an isomerization zone. This contacting, which occurs in a hydrogen admixture, may be effected using the catalyst in a fixed-bed system, a moving-bed system, a fluidized bed system, or in a batch type operation. In view of the danger of catalyst attrition loss and of operational advantages, it is preferred to use a fixed-bed system. In this system, a hydrogen gas and the feedstock are preheated by suitable heating means to the desired reaction temperature and then passed into an isomerization zone containing a fixed bed of catalyst. The isomerization conversion zone may be one or more separate reactors with suitable means therebetween to ensure that the desired isomerization temperature is maintained at the entrance to each zone. The reactants may be contacted with the catalyst in the upward, downward, or radial fashion. Further, the reactants may be in a liquid phase, vapor phase, or a vapor/liquid phase when contacting the catalyst.

Suitable isomerization conditions include a temperature of about 0°-600° C., preferably 350°-500° C., a pressure of about 1-100 atmospheres, preferably 2-30 atmospheres, a hydrogen to hydrocarbon mole ratio of about 0.5:1 to about 15:1, and a liquid hourly space velocity of about 0.5-30 $hr^{-1}$.

An essential feature of the present invention is manipulating the isomerization conditions to effect high severity operations during the pretreatment step and moderate severity operations during the normal mode of operations. The operating conditions that can be manipulated to effect such operations are ethylbenzene conversion, isomerization reactor inlet temperature, hydrogen to hydrocarbon mole ratio, or any combination thereof.

In accordance with the present invention, ethylbenzene conversion is defined as the amount of ethylbenzene entering the isomerization reactor minus the amount of ethylbenzene exiting the isomerization reactor divided by the amount of ethylbenzene entering the isomerization reactor.

In a preferred embodiment, ethylbenzene conversion is defined in terms of the amount of ethylbenzene in the $C_8$ aromatic feedstream and the amount of ethylbenzene exiting a deheptanizer. The function of the deheptanizer is to reject light reaction by-products in the net overhead stream while recovering all $C_8$ aromatics in the deheptanizer net bottom stream. Most of the toluene by-product is removed in the deheptanizer net overhead stream. It is important to reject all of the benzene and as much toluene as possible in the deheptanizer net overhead stream to avoid recycling these materials to the para-xylene separation unit. Accordingly, in this embodiment, ethylbenzene conversion is defined as:

$$EBC = \left[1 - \frac{(EB_P \cdot P + EB_B \cdot B)}{EB_F \cdot F}\right] \cdot 100\%$$

where:
$EB_F$ = weight % ethylbenzene in the feedstock
$EB_P$ = weight % ethylbenzene in the deheptanizer net overhead liquid
$EB_B$ = weight % ethylbenzene net bottoms F = reactor feedstock mass rate
P = deheptanizer net overhead liquid mass rate
B = deheptanizer net bottoms mass rate In one embodiment of the present invention, the high severity conditions of the pretreatment step are effected by operating at a relatively high ethylbenzene conversion, preferably greater than about 80%, more preferably greater than about 85%, most preferably greater than 90%. In contrast, the moderate severity conditions of the second step (normal operation mode) are effected by operating at relatively low ethylbenzene conversion, preferably less than about 80%, most preferably less than about 65%. It is undesirable to operate at ethylbenzene conversions over 65% for an extended period of time because generally xylene losses are directly proportional to increases in ethylbenzene conversion.

Ethylbenzene conversion can be varied by manipulating the operating temperature to the reactor. Accordingly, in one embodiment of the present invention, the desired ethylbenzene conversion is effected by operating at a relatively high reactor inlet temperature, preferably greater than about 390° C., more preferably greater than about 400° C. In contrast, the moderate severity conditions of the second step (normal operation mode) are effected by operating at a relatively low reactor inlet temperature, preferably not more than about 385° C. It is undesirable to operate at a reactor inlet temperature of greater than about 400° C. for an extended period of time because generally xylene losses are directly proportional to increases in reactor inlet temperature.

In another embodiment of the present invention, the desired ethylbenzene conversion can be effected by operating at a relatively low hydrogen to hydrocarbon mole ratio, preferably lower than about 2.0, more preferably lower than about 1. In contrast, the moderate severity conditions of the second step (normal operation mode) are effected by operating at a relatively high hydrogen to hydrocarbon mole ratio, preferably higher than about 4. It is undesirable to operate at a hydrogen to hydrocarbon mole ratio of lower than 1 for an extended period of time because generally xylene losses are directly proportional to decreases in hydrogen to hydrocarbon mole ratio.

For the purposes of the present invention, the hydrogen to hydrocarbon mole ratio can generally be calculated using the following expression:

$$H_2/HC = \frac{RG \cdot H_2pur \cdot (MW_{RG}/28.696) \cdot 1.292 \times 10^{-3}}{(F \cdot p_F/MW_F)}$$

where:
RG = recycle gas rate, $Nm^3/h$
$MW_{RG}$ = recycle gas molecular weight
$H_2pur$ = mole fraction of hydrogen in recycle gas
F = liquid charge rate to the reactor, $m^3/h$
$P_F$ = density of liquid charge at 15.6° C., $Kg/m^3$
$MW_F$ = molecular weight of liquid charge In the pretreatment step of the present invention, the high severity isomerization conditions are maintained for a period of time sufficient to deposit a substantial amount of carbonaceous material on the isomerization catalyst. In a preferred embodiment, the catalyst resulting from the pretreatment step of the present invention has a carbon content of at least about 0.1 wt. %, more preferably at least about 0.2 wt. %, most preferably at least about 0.3 wt. %. The time period for the high ethylbenzene conversion pretreatment mode of operation can range from about 10–24 hours. It is important not to go beyond the 24 hours because this can result in increased xylene losses due, for example, to cracking of $C_8$ aromatics.

EXAMPLE

The objective of this example was to test an isomerization catalyst using a high severity startup or pretreatment procedure and evaluate the effects of such a pretreatment on the isomerization xylene losses occurring during normal mode of operation. The data showed that a $C_8$ isomerization process that was operated at high severity conditions (e.g., at 90% ethylbenzene conversion) for a period of not more than 24 hours exhibited substantially better lined-out selectivity performance (i.e. xylene retention) as opposed to the runs that were started up at moderate conditions (e.g., about 65% ethylbenzene conversion).

In this test, a $C_8$ aromatic feedstock was charged to a small reactor. The feed blend used is characterized by Table 1 below:

TABLE 1

| Component | Wt. % |
| --- | --- |
| $C_8$ Naphthene | 0.1 |
| Ethylbenzene | 6.6 |
| Para-xylene | 1.0 |
| Meta-xylene | 70.9 |
| Ortho-xylene | 21.4 |
| $C_9$ Paraffin | — |

This feed blend was charged into a blend pot to which 30 cc of water was added to maintain a concentration of about 300 wt. ppm water. The feed in the blend pot was kept recirculating and was used to fill the charge tank. The feed was then pumped through a flow controlling device which was enclosed in a chilled glycol bath.

The feed was combined with hydrogen and then was introduced into the top of the reactor. The reactor was a 52 inch stainless steel cylindrical tube having a diameter of 7/8 inches. At the top of the reactor was a thermocouple for measuring the temperature of the feed blend as it entered the reactor. The reactor was loaded with glass wool above and below the catalyst bed.

The catalyst bed consisted of 27.65 grams of an isomerization catalyst containing platinum and lead composited with a pentasil zeolite.

The effluent from the reactor was routed to a high pressure separator, where off-gas was released, admixed with fresh make-up hydrogen, which was controlled and measured by a thermal mass flow meter, passed through a dryer, and recycled back to the reactor. The separator bottoms were directed to a debutanizer column. Liquid product was collected in a graduated cylinder immersed in an ice bath. Product light ends were released to a bubbler, measured with a wet test meter, and vented.

The FIGURE is a plot of ethylbenzene conversion versus xylene losses. Xylene losses were calculated using the following equation:

$$XL_1 = \frac{X_F \cdot F - (X_p \cdot P + X_B B)}{X_F \cdot F} * 100\%$$

where:
$X_F$ = wt. % total xylene in the feed
F = total feed flow rate, MT/h
$X_P$ = total xylenes in the debutanizer bottoms
P = total debutanizer bottoms flow rate, MT/h $X_B$ = total xylenes in the debutanizer overhead
B = total debutanizer overhead flow rate, MT/h Plotted in the FIGURE are three reference runs (Nos. 1–3) and one run using the process of the present invention (No. 4). All of the runs used the equipment and catalyst described hereinabove. Run No. 1 was a reference run that was operated under the following conditions: a startup temperature of 384° C., a normal mode of operation temperature of 377°–396° C., a pressure of 175 psig, a hydrogen to hydrocarbon mole ratio of 4.0, a liquid hourly space velocity of 3.0, and a pretreatment period of about 24 hours. Run No. 2 was also a reference run that was operated under the following conditions: a startup temperature of 379° C., a normal mode of operation temperature of 368°–397° C., a pressure of 175 psig, a hydrogen to hydrocarbon mole ratio of 4.0, a liquid hourly space velocity of 3.0, and a pretreatment period of about 24 hours. Run No. 3 was another reference run that was operated under the following conditions: a startup temperature of 378° C., a normal mode of operation temperature of 378°–390° C., a pressure of 175 psig, a hydrogen to hydrocarbon mole ratio of 4.0, a liquid hourly space velocity of 3.0, and a pretreatment time of about 24 hours. Run No. 4 used the present invention. In Run No. 4, the operating conditions were as follows: a startup temperature of 404° C., a normal mode of operation temperature of 382°–404° C., a pressure of 175 psig, a hydrogen to hydrocarbon mole ratio of 4.0, and a liquid hourly space velocity of 3.0, and a pretreatment time of about 24 hours.

A key difference between the reference runs (Run Nos. 1–3) and the run representing the present invention (Run No. 4) is the start-up ethylbenzene conversion. In Run Nos. 1–3, the start-up ethylbenzene conversions were 69.3%, 69.6%, 61.0%, respectively. In Run No. 4, the start-up ethylbenzene conversion was 90.9%. Another related difference between the reference runs and the run representing the present invention was the start-up temperature. In Run Nos. 1–3, the start-up temperatures were 384° C., 379° C., and 378° C., respectively. In Run No. 4, the start-up temperature was 404° C.

With respect to the FIGURE, it can be seen that xylene losses increase with increasing ethylbenzene conversion. Nevertheless, a comparison of the reference runs (Run Nos. 1–3) with the pretreatment procedure of the present invention (Run No. 4) shows that the data depicted by the asterisks, which are representative of the present invention, fall below that of the data depicted by the boxes, triangles, and circles which are representative of the reference runs. In other words, the run that was started up at high severity conditions exhibited substantially better lined-out selectivity performance as opposed to the runs that were started up at moderate conditions.

What is claimed is:

1. A method of isomerizing $C_8$ aromatics to a product stream comprising xylenes, which comprises the steps of:
   (a) introducing a $C_8$ aromatic feedstock comprising a nonequilibrium mixture of at least one xylene isomer in admixture with ethylbenzene into an isomerization zone in the presence of an isomerization catalyst under isomerization conditions sufficient to result in an ethylbenzene conversion of at least about 80% for a period of time sufficient to deposit a carbon content of at least about 0.1 wt. % on said catalyst;
   (b) continuing to contact said $C_8$ aromatic feedstock in said isomerization zone in the presence of the catalyst resulting from step (a) under isomerization conditions sufficient to result in an ethylbenzene conversion of not more than about 65%; and
   (c) recovering said product stream.

2. The method of claim 1 wherein the catalyst resulting from step (a) has a carbon content of at least about 0.2 wt. %.

3. The method of claim 1 wherein the catalyst resulting from step (a) has a carbon content of at least about 0.3 wt. %.

4. The method of claim 1 wherein in step (a) said ethylbenzene conversion is at least about 90%.

5. The method of claim 1 wherein in step (a) said isomerization conditions comprise a temperature of at least about 400° C. and wherein in step (b) said isomerization conditions comprise a temperature of not more than about 385° C.

6. The method of claim 1 wherein in step (a) said isomerization conditions include a hydrogen to hydrocarbon mole ratio of less than about 2 and wherein in step (b) said isomerization conditions include a hydrogen to hydrocarbon mole ratio of greater than about 4.

7. The method of claim 1 wherein in step (a) said period of time is about 10–24 hours.

8. A method for isomerizing $C_8$ aromatics into a product stream comprising xylenes, which comprises the steps of:
   (a) introducing a $C_8$ aromatic feedstock comprising a nonequilibrium mixture of xylene isomers in admixture with ethylbenzene into an isomerization zone in the presence of an isomerization catalyst under isomerization conditions sufficient to to result in an ethylbenzene conversion of at least about 90% for a period of time sufficient to deposit a carbon content of at least about 0.1 wt % on said catalyst;
   (b) continuing to contact said $C_8$ aromatic feedstock in said isomerization zone in the presence of the catalyst resulting from step (a) under isomerization conditions sufficient to result in an ethylbenzene conversion of not more than about 65%; and
   (c) recovering said product stream.

9. The method of claim 8 wherein said ethylbenzene conversion is at least about 90%.

10. The method of claim 8 wherein in step (a) said isomerization conditions include a temperature of at least about 400° C. and wherein in step (b) said isomerization conditions include a temperature of not more than about 385° C.

11. The method of claim 8 wherein in step (a) said isomerization conditions include a hydrogen to hydrocarbon mole ratio of less than about 2 and wherein in step (b) said isomerization conditions include a hydrogen to hydrocarbon mole ratio of greater than about 4.

12. The method of claim 8 wherein in step (a) said period of time is about 10–24 hours.

13. The method of claim 8 wherein the catalyst resulting from step (a) has a carbon content of at least about 0.2 wt. %.

14. The method of claim 8 wherein said isomerization catalyst comprises a Group VIII metal and a lead component deposited on a zeolite composite support.

15. A method for isomerizing $C_8$ aromatics to a product stream comprising xylenes comprising the steps of:
   (a) introducing a $C_8$ aromatic feedstock comprising a nonequilibrium mixture of xylene isomers in admixture with ethylbenzene into an isomerization zone in the presence of a catalyst comprising a Group VIII metal and a lead component deposited on a zeolite composite support under isomerization conditions sufficient to effect an ethylbenzene conversion of at least about 80% for 10–24 hours to deposit at least about 0.1 wt. % carbon on said catalyst;

(b) continuing to contact said $C_8$ aromatic feedstock in said isomerization zone in the presence of the catalyst resulting from step (a) under isomerization conditions sufficient to effect an ethylbenzene conversion of less than about 65%; and (c) recovering said product stream.

16. The method of claim 15 wherein in step (a) said ethylbenzene conversion is at least about 90%.

17. The method of claim 15 wherein in step (a) said isomerization conditions include a temperature of at least about 400° C. and wherein in step (b) said isomerization conditions include a temperature of not more than about 385° C.

18. The method of claim 15 wherein in step (a) said isomerization conditions include a hydrogen to hydrocarbon mole ratio of less than about 2 and wherein in step (b) said isomerization conditions include a hydrogen to hydrocarbon mole ratio of greater than about 4.

19. The method of claim 15 wherein the catalyst resulting from step (a) has a carbon content of at least about 0.2 wt. %.

20. A method for isomerizing $C_8$ aromatics to a product stream comprising xylenes comprising the steps of:

(a) introducing a $C_8$ aromatic feedstock comprising a nonequilibrium mixture of xylene isomers in admixture with ethylbenzene into an isomerization zone in the presence of catalyst comprising a combination of a Group VIII metal component and a lead component deposited on a carrier comprising a pentasil zeolite and an inorganic oxide binder under isomerization conditions sufficient to effect an ethylbenzene conversion of at least 90% for 10–24 hours to deposit at least about 0.2 wt. % carbon on said catalyst;

(b) continuing to contact said $C_8$ aromatic feedstock in said isomerization zone in the presence of the catalyst resulting from step (a) under isomerization conditions sufficient to effect an ethylbenzene conversion of not more than about 65%; and (c) recovering said product stream.

21. The method of claim 20 wherein in step (a) said isomerization conditions include a temperature of at least about 400° C. and wherein in step (b) said isomerization conditions include a temperature of not more than about 385° C.

22. The method of claim 20 wherein in step (a) said isomerization conditions include a hydrogen to hydrocarbon mole ratio of less than about 2 and wherein in step (b) said isomerization conditions include a hydrogen to hydrocarbons ratio of greater than about 4.

* * * * *